US011918962B2

(12) United States Patent
Warren

(10) Patent No.: US 11,918,962 B2
(45) Date of Patent: Mar. 5, 2024

(54) PROPPANT CONCENTRATION ACCURACY IN A FRACTURING FLUID BY COMPENSATING FOR PROPPANT MOISTURE

(71) Applicant: Halliburton Energy Services, Inc., Houston, TX (US)

(72) Inventor: Wesley John Warren, Fort Worth, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 201 days.

(21) Appl. No.: 17/443,147

(22) Filed: Jul. 21, 2021

(65) Prior Publication Data
US 2023/0032405 A1 Feb. 2, 2023

(51) Int. Cl.
*B01F 23/50* (2022.01)
*B01F 35/21* (2022.01)
(Continued)

(52) U.S. Cl.
CPC ............... *B01F 23/51* (2022.01); *B01F 23/59* (2022.01); *B01F 35/2111* (2022.01);
(Continued)

(58) Field of Classification Search
CPC .......... C09K 8/805; C09K 8/80; C09K 8/575; E21B 43/26; E21B 43/267; E21B 43/2607; E21B 21/062
See application file for complete search history.

(56) References Cited

U.S. PATENT DOCUMENTS

| 5,590,976 A | 1/1997 | Kilheffer et al. |
| 2019/0144216 A1 | 5/2019 | Dawson et al. |
| 2020/0032136 A1* | 1/2020 | Nguyen ............... E21B 43/13 |

FOREIGN PATENT DOCUMENTS

| CA | 2989826 C * | 5/2020 | ............ C01F 7/066 |
| WO | 2020027796 A1 | 2/2020 | |

OTHER PUBLICATIONS

English translation of CN 102753501 (Year: 2012).*

* cited by examiner

*Primary Examiner* — Zakiya W Bates
(74) *Attorney, Agent, or Firm* — K&L Gates LLP

(57) ABSTRACT

A method of determining a dry proppant concentration in a fracturing fluid includes combining a wet proppant with a carrier fluid in a mixer to form the fracturing fluid. The dry proppant concentration of the fracturing fluid leaving the mixer is determined using a moisture content of the wet proppant entering the mixer, wherein use of the moisture content prevents overestimation of the dry proppant concentration. The method can be preformed using a system for injecting fracturing fluid into a borehole, the fracturing fluid including a carrier fluid mixed with a wet proppant including a dry proppant dampened with a dampening liquid. The system includes a mixer operable to receive and mix the carrier fluid and the wet proppant to form the fracturing fluid, a frac pump operable to inject the fracturing fluid into the borehole, and a control system comprising a processor operable to receive a moisture content of the wet proppant before being mixed with the carrier fluid and programmed to determine a dry proppant concentration of the fracturing fluid formed in the mixer using a moisture content of the wet proppant, wherein use of the moisture content prevents overestimation of the dry proppant concentration.

20 Claims, 4 Drawing Sheets

(51) Int. Cl.
*B01F 35/22* (2022.01)
*B01F 35/221* (2022.01)
*B01F 101/49* (2022.01)
*E21B 43/26* (2006.01)
*E21B 43/267* (2006.01)
*G01N 9/00* (2006.01)
*G01N 33/28* (2006.01)

(52) U.S. Cl.
CPC ...... *B01F 35/2132* (2022.01); *B01F 35/2134* (2022.01); *B01F 35/2135* (2022.01); *B01F 35/2202* (2022.01); *B01F 35/2203* (2022.01); *B01F 35/2211* (2022.01); *E21B 43/2607* (2020.05); *E21B 43/267* (2013.01); *G01N 9/00* (2013.01); *G01N 33/2823* (2013.01); *B01F 23/581* (2022.01); *B01F 2101/49* (2022.01)

PROPPANT CONCENTRATION ACCURACY IN A FRACTURING FLUID BY COMPENSATING FOR PROPPANT MOISTURE

BACKGROUND

This section is intended to provide relevant background information to facilitate a better understanding of the various aspects of the described embodiments. Accordingly, these statements are to be read in this light and not as admissions of prior art.

It is often desirable to treat a wellbore or a subterranean formation with various types of treatment fluids designed to resolve a specific wellbore or reservoir condition in an effort to produce oil or gas from a reservoir. For example, stimulation is a treatment performed on a well to restore or enhance the productivity of the well. Stimulation treatments include, for example, hydraulic fracturing.

Fracturing treatments are performed above the fracture pressure of the reservoir formation and create a highly conductive flow path between the reservoir and the wellbore. During a fracturing treatment, proppant is placed downhole by flowing as part of a fracturing fluid. However, the amount of proppant used can be expensive and there is a continued push to decrease the cost of proppant used for well stimulation. In some cases, the sand is locally mined and the step of drying the sand has been eliminated. The only drying may be from decanting (allowing the sand to naturally drain and air dry in a pile) which can lead to a range of moisture rates. Some operators have reported moisture rates ranging from 6% to 11% by weight. The use of wet sand can significantly reduce cost, but it causes new operational challenges surrounding the fracture fluid blending process.

In addition, to reduce risk to personnel and the environment, there has been a push to remove radioactive (RA) densometers from fracture fluid blending equipment. Traditionally the RA densometer was used to measure the sand concentration delivered by the blender. In place of the radioactive densometer, the sand concentration is now often measured by comparing the flowmeters measuring fluid flow rate of clean fluid (fluid substantially free of proppant) into the mixer and slurry flow rate leaving the mixer. This calculation is sensitive to accurate measurement of both rates and does not account for fluid being introduced through the proppant stream. If the dampening liquid content of the wet proppant is not accounted for, a significant error (in the range of 30-50% based on typical operational parameters) will result in the calculated sand concentration from the flowmeters. If the moisture content is not taken into account, the sand concentration calculation underestimates the liquid rate and overestimates the proppant rate (and thus the mass rate of dry proppant), leading to a calculated proppant concentration that is erroneously high and unnecessarily expensive as well as potentially less effective in the fracturing treatment, causing lowered permeability and recovery within a subterranean formation.

BRIEF DESCRIPTION OF THE DRAWINGS

Embodiments are described with reference to the following figures. The same or sequentially similar numbers are used throughout the figures to reference like features and components. The features depicted in the figures are not necessarily shown to scale. Certain features of the embodiments may be shown exaggerated in scale or in somewhat schematic form, and some details of elements may not be shown in the interest of clarity and conciseness.

DETAILED DESCRIPTION

In this description, "concentration" is the concentration of a substance, expressed in units of lbs/gal. In this description, "flow rate" is either or both the volumetric flow rate or mass flow rate of a fluid or mixture at a particular location, expressed in units of gal/min, or gpm, or kg/sec.

The present disclosure describes methods of and systems for improving proppant concentration and density accuracy in a fracturing fluid by compensating for proppant moisture. The methods and systems measure a moisture content of the proppant entering a mixer and combine the measurement with a measured carrier fluid flow rate into the mixer and a discharge flow rate of the fracturing fluid after the mixer to accurately calculate proppant concentration for wet proppant applications. A fracturing fluid density of the fracturing fluid after the mixer is also determined. A moisture sensor installed on either the blender at the proppant inlet or on the proppant metering device may be used to indicate percent moisture by either weight or volume for the proppant entering the mixer. The output from the moisture sensor is combined with the measured clean and discharge flow rates to calculate proppant concentration and density accurately. Alternatively, the percent moisture content may be inputted by a user. In this way, an RA densometer useful for measuring proppant concentration is not needed and the accuracy of the determination proppant concentration in and density of the fracturing fluid is improved. The methods and systems can also be used to validate proppant concentration values supplied by a third party proppant metering device without directly measuring delivery rate from that proppant metering device.

The methods and systems are used as part of a fracturing treatment where wet proppant is combined with a carrier fluid in a mixer to produce a fracturing fluid. The fracturing fluid is then injected into a borehole at a pressure to produce the conductive flow paths between the downhole reservoir and the borehole. The proppant concentration in and density of the fracturing fluid are determined as described using a control system. Then, as needed, the control system can adjust the flow rate of the wet proppant entering the mixer based on the determined dry proppant concentration or density as needed to produce the desired dry proppant concentration in the fracturing fluid.

Figure 1:
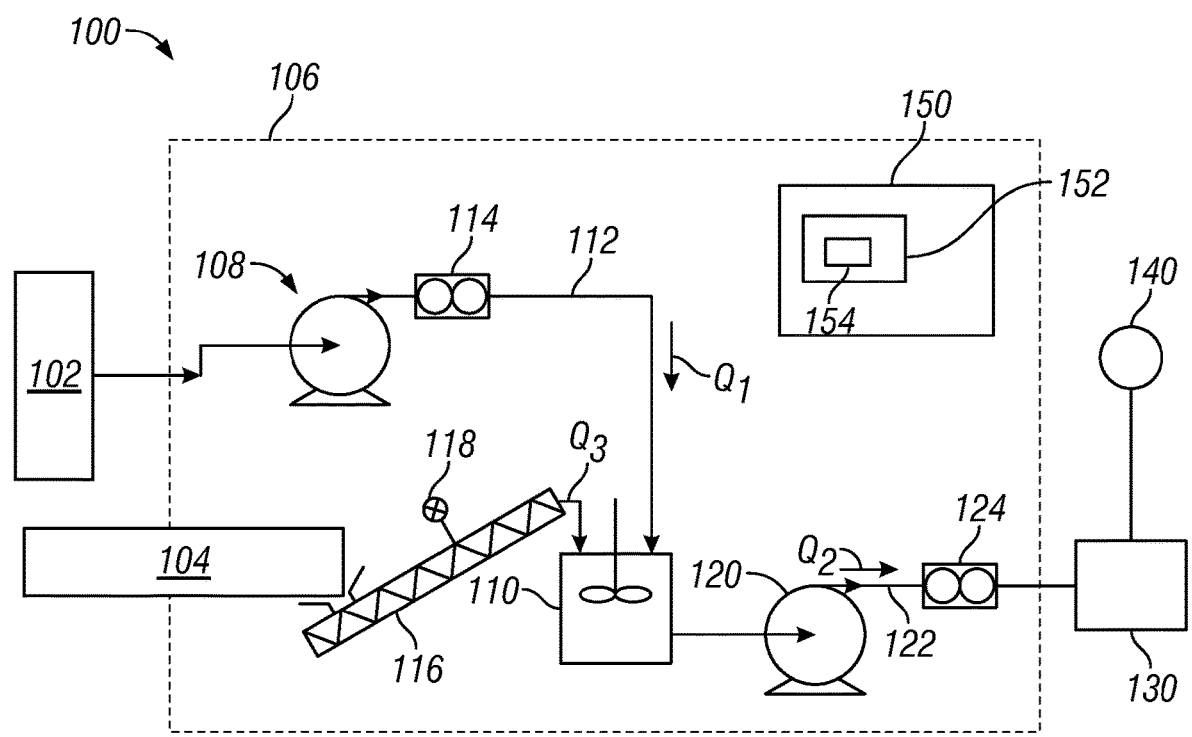
FIG. 1 is a block diagram of an embodiment of a treatment assembly used for conducting a treatment operation such as a fracturing operation.

Turning now the figures, FIG. 1 is a block diagram of an embodiment of a treatment assembly 100 used for conducting a treatment operation such as a fracturing operation. The treatment assembly 100 includes a "clean" fluid supply 102 for supplying a clean carrier fluid substantially free of any proppant. As used herein a "fluid" is a continuous amorphous substance that tends to flow and to conform to the outline of its container as a liquid or a gas, when tested at a temperature at room temperature of 68° F. (20° C.) and standard pressure (1 atm). The carrier fluid can be a water-based fluid. As used herein, "water-based" means that the fluid comprises greater than 50% by weight an aqueous solution. In general, as used herein, an "aqueous solution" refers to a water used or received to be used in any of the described methods. The water is referred to as an "aqueous solution" because it would be expected to normally include substantial or insubstantial rates of dissolved solids, such as sodium chloride, calcium chloride, magnesium chloride, sodium sulfate, and other water-soluble salts (up to the saturation limit of each). The term "aqueous solution" may include small amounts of other materials, however, the term excludes anything that is included in or added to the aqueous solution for the purposes of a treatment operation in which the aqueous solution is to be used. For example, an "aqueous solution" may be up to 1% by weight of total water-miscible or water-soluble organic materials; up to 2% by weight of total dispersed, oil, grease, and water-insoluble production chemicals; up to 10% by weight of total dispersed oil, grease, and non-surfactant water-insoluble production chemicals with surfactant production chemicals; and up to 1% by weight of total suspended silt or smaller particles (avoiding any layer of oil or other insoluble materials floating on the surface or any sludge settled on the bottom of the water as received). For example, the oil, grease, and production chemicals would be typically found, for example, in produced water. A water-based fluid (comprising an aqueous solution) may or may not include other suspended components, such as oil, clay, proppant, and other additives, which can be added to or mixed with the aqueous solution for the purposes of forming a base fluid or treatment fluid. A water-based fluid can be an emulsion, foamed with a gas, or both. For example, such suspended components can be selected from the group consisting of: a clay, a water-insoluble organic material, a gas, and any combination thereof in any proportion. Further, a water-based fluid may include other water-soluble or water-miscible additives. The carrier fluid from the clean fluid supply 102 may include chemicals or additives that have been added to the aqueous solution to enhance the properties of the fracturing fluid. There also may be additional additives added to the fluid between where the fluid leaves the clean fluid supply 102 and where the carrier fluid enters the mixer 110. This would still be considered "clean" fluid as the term "clean" fluid means that the fluid is substantially free of proppant.

The treatment assembly 100 also includes a wet proppant supply 104 for supplying proppant that may be dampened with a dampening liquid. The wet proppant supply 104 is a supply of wet proppant provided to the treatment assembly 100. As used herein, "proppant" includes particles mixed with a carrier fluid to form a fracturing fluid to hold fractures open after a fracturing treatment. Suitable proppant may include naturally occurring sand grains, but man-made or specially engineered proppant, such as resin-coated sand or high-strength ceramic material, may also be used. The dampening liquid, while may primarily be water, may be any other type of liquid added to dry proppant to form the wet proppant and may also include a salt or other additive to inhibit freezing.

Both the carrier fluid and the wet proppant are supplied to a blending system 106 for blending the carrier fluid and the wet proppant into a fracturing fluid. The carrier fluid is pumped into the blending system 106 with a suction pump 108, which then pumps the carrier fluid into a mixer 110 through a conduit 112. Positioned at the suction pump 108 or within the conduit 112 is a flowmeter 114 operable to measure a flow rate $Q_1$ of the carrier fluid entering the mixer 110.

The wet proppant is moved by a proppant metering device 116, such as proppant screws, which delivers the wet proppant to the mixer 110 to be mixed with the carrier fluid to form the fracturing fluid. The proppant metering device is controllable to control the rate $Q_3$ of wet proppant delivered into the mixer 110, which will be discussed in further detail below. A moisture sensor or meter 118 may be installed on the proppant metering device 116 and is operable to determine a percent moisture by either weight or volume for the proppant entering the mixer 110. Alternatively, the moisture meter 118 may be installed at any point suitable to measure the percent moisture of the wet proppant before the wet proppant enters the mixer 110. The moisture meter 118 may be any suitable type of moisture meter, such as a near infrared sensor, a microwave sensor, or other sensors based on measuring resistivity or capacitance. Alternatively, the percent moisture content by either weight or volume may be inputted by a user.

With the wet proppant and the carrier fluid added to the mixer 110, the mixer 110 mixes the wet proppant and the carrier fluid together into a fracturing fluid. The mixer 110 can be a mixing tub, which is open to atmosphere, a centrifugal mixer, or any other mixer suitable for mixing the wet proppant with the carrier fluid. The mixer 110 may also be self-regulating to maintain nearly a constant volume of components within the mixing tub. The bending system 106 further includes a discharge pump 120, which pumps the fracturing fluid out of the mixer 110 and out of the blending system 106 to one or more frac pumps 130 through a conduit 122. Positioned at the discharge pump 120 or within the conduit 122 is a flowmeter 124 operable to measure a flow rate $Q_2$ of the fracturing fluid flowing from the discharge pump 120 to the frac pumps 130. Alternatively, multiple flowmeters 124 may be located and operable to measure the flow rate outputs of the frac pumps 130 and the flow rate $Q_2$ determined by summing the measured flow rate outputs of the frac pumps 130. The frac pumps 130 then pump the fracturing fluid into the borehole 140, typically through a wellhead, for delivery to the subterranean formation at pressure to create the conductive flow paths in the formation.

The treatment assembly 100 and operation thereof can be carried out using a computer-operated control system 150. Such a control system 150 is in communication with various sensors and meters, such as the flowmeters, 114, 124 and the moisture meter 118. The control system 150 may be in communication with other sensors and meters as well, such as the temperature sensors, pressure sensors, flowmeters, and other devices configured to measure a variable output. The control system 150 includes a computer 152, which includes a processor 154. As mentioned above, the proppant metering device 116 is controllable to control the rate $Q_3$ of wet proppant delivered to the mixer 110. The control system 150 uses information received by the sensors or users and meters to determine the actual amount of proppant, or dry proppant, in the wet proppant and controls the wet proppant delivery rate $Q_3$ based on a desired dry proppant concentration or density in the fracturing fluid to be injected in the borehole 140. To do so, the control system 150 uses the computer 152 and the processor 152 to determine the dry proppant concentration in the fracturing fluid using the inputted or measured moisture content from the moisture meter 118. Doing so prevents overestimation of the dry proppant concentration and thus prevents using too much proppant in the fracturing fluid than is desired.

To determine the dry proppant concentration using moisture content by volume of the proppant entering the mixer 110, the processor 154 is programmed to determine a total flow rate of the wet proppant (dry proppant plus dampening liquid) by volume $Q_{3vol}$ entering the mixer 110 by subtracting the volumetric flow rate of the carrier fluid $Q_{1vol}$ of clean fluid entering the mixer from the volumetric flow rate of the fracturing fluid $Q_{2vol}$ leaving the mixer 110 according to the following equation:

$$Q_{3vol} = Q_{2vol} - Q_{1vol} \quad \text{(Eq. 1)}$$

Eq. 1 assumes that the mixer 110 is at constant volume. However, if not constant volume, then Eq. 1 is modified to account for volumetric rate of change $Q_{Mvol}$ within the mixer 110 according to the following:

$$Q_{3vol} = Q_{2vol} - (Q_{1vol} + Q_{Mvol}) \quad \text{(Eq. 2)}$$

where $Q_{Mvol}$ is determined according to the following:

$$Q_{Mvol} = \pi (r_M)^2 (h_M) \quad \text{(Eq. 3)}$$

In Eq. 3, $r_M$ is the radius of the cylindrical mixing tub and is input by an operator. $h_M$ is the rate of change of fluid height in the mixer 110 and can be determined by a fluid level sensor (not shown) in mixer 110. Eqs. 2 and 3 assume the mixer tub is cylindrical. However, volume can be calculated by fluid level for any mixer shape with an appropriate relationship of volume to fluid level. The relationship can be determined by creating a lookup table of mixer volume vs level sensor output. An initially empty mixer is filled while measuring volume added using the flowmeter 114. The relationship is then determined using the lookup table.

The determined $Q_{3vol}$ is then converted to a flow rate of the dry proppant $Q_{3Pvol}$ by first determining the flow rate of the dampening fluid $Q_{3Fvol}$ according to the following:

$$Q_{3Fvol} = MC_{vol} * Q_{3vol} \quad \text{(Eq. 4)}$$

where $MC_{vol}$ is % moisture content by volume of the wet proppant as either measured by the moisture meter 118 or entered by an operator. Moisture is defined as surface moisture and liquid between the proppant particles, not liquid within the proppant particles themselves. AVF is the absolute volume factor for the proppant and DF is the density of the dampening liquid on the wet proppant, both of which are input by an operator.

$Q_{3vol}$ and $Q_{3Fvol}$ are then used to calculate the volumetric flow rate of the dry proppant $Q_{3Pvol}$ according to the following:

$$Q_{3Pvol} = Q_{3vol} - Q_{3Fvol} \quad \text{(Eq. 5)}$$

A concentration of solids by volume $C_{vol}$ is then determined according to the following:

$$C_{vol} = Q_{3Pvol} / Q_{2vol} \quad \text{(Eq. 6)}$$

The dry proppant concentration $PC_{vol}$ of the fracturing fluid leaving the mixer 110 is then determined according to the following:

$$PC_{vol} = C_{vol} / ((1 - C_{vol}) * AVF) \quad \text{(Eq. 7)}$$

AVF indicates the volume of liquid displaced per pound of dry proppant in units of gal liquid/lb proppant. It should be appreciated that proppant particle density is the reciprocal of AVF and therefore proppant particle density may be used instead of AVF in Eq. 7. It should be appreciated that proppant particle density is the reciprocal of AVF and therefore proppant particle density may be used instead of AVF in Eq. 7.

To determine the dry proppant concentration using moisture content by weight of the proppant entering the mixer 110, the processor 154 is programmed to determine a total flow rate of the wet proppant (dry proppant plus dampening liquid) $Q_3$ entering the mixer 110 by subtracting the volumetric flow rate of the carrier fluid $Q_1$ of clean fluid entering the mixer from the flow rate of the fracturing fluid $Q_2$ leaving the mixer 110 according to the following equation:

$$Q_3 = Q_2 - Q_1 \quad \text{(Eq. 8)}$$

It should be appreciated that the calculation method may be used based on flow rates by volume, mass, or weight of the materials and therefore, all flow rates in Equations 8-20 may be either. Further, Eq. 8 assumes that the mixer 110 is at constant volume. However, if not constant volume, then Eq. 8 is modified to account for rate of change of liquid $Q_M$ within the mixer 110 according to the following:

$$Q_3 = Q_2 - (Q_1 + Q_M) \quad \text{(Eq. 9)}$$

where $Q_M$ is determined according to the following:

$$Q_M = \pi (r_M)^2 (h_M) \quad \text{(Eq. 10)}$$

In Eq. 10, $r_M$ is the radius of the cylindrical mixing tub and is input by an operator. $h_M$ is the rate of change of fluid height in the mixer 100 and can be determined by a fluid level sensor (not shown) in mixer 110. Eqs. 9 and 10 assume the mixer tub is cylindrical. However, volume can be calculated by fluid level for any mixer shape with an appropriate relationship of volume to fluid level. The relationship can be determined by creating a lookup table of mixer volume vs level sensor output. An initially empty mixer is filled while measuring volume added using the flowmeter 114. The relationship is then determined using the lookup table.

The determined $Q_3$ is then converted to a volumetric flow rate of the dry proppant $Q_{3P}$ by first determining the volumetric flow rate of the dampening fluid $Q_{3F}$ according to the following:

$$Q_{3F} = (Q_3 * MC_{wt}) / (MC_{wt} + DF * AVF (1 - MC_{wt})) \quad \text{(Eq. 11)}$$

where $MC_{wt}$ is % moisture content by weight of the wet proppant as either measured by the moisture meter 118 or entered by an operator. Moisture is defined as surface moisture and liquid between the proppant particles, not liquid within the proppant particles themselves. AVF is the absolute volume factor for the proppant and DF is the density of the dampening liquid on the wet proppant, both of which are input by an operator. AVF indicates the volume of liquid displaced per pound of dry proppant in units of gal liquid/lb proppant. It should be appreciated that proppant particle density is the reciprocal of AVF and therefore proppant particle density may be used instead of AVF in Eq. 11.

$Q_3$ and $Q_{3F}$ are then used to calculate the volumetric flow rate of the dry proppant $Q_{3P}$ according to the following:

$$Q_{3P} = Q_3 - Q_{3F} \quad \text{(Eq. 12)}$$

$MR_{DP}$, the mass flow rate of the dry proppant entering the mixer 110, can then be determined according to the following:

$$MR_{DP} = Q_{3P} / AVF \quad \text{(Eq. 13)}$$

It should be appreciated that proppant particle density is the reciprocal of AVF and therefore proppant particle density may be used instead of AVF in Eq. 13.

The mass flow rate of the dampening fluid, $MR_{3F}$, can then be determined according to the following:

$$MR_{3F} = Q_{3F} * DF \quad \text{(Eq. 14)}$$

Further, the mass flow rate from the suction pump, $MR_1$, can be determined according to the following:

$$MR_1 = Q_1 * D_1 \quad \text{(Eq. 15)}$$

wherein $D_1$ is the density of the clean carrier fluid entering the suction pump 108.

The density of the combined fluids flowing into the mixer 110, $D_{CL}$, can then be determined according to the following:

$$D_{CL} = (MR_1 + MR_{3F})/(Q_1 + Q_{3F}) \quad \text{(Eq. 16)}$$

The concentration of solids by weight, $C_w$, in the fracturing fluid leaving the mixer 110 can then be determined according to the following:

$$C_{wt} = MR_{DP}/(MR_{DP} + MR_{3F} + MR_1) \quad \text{(Eq. 17)}$$

The dry proppant concentration by weight $PC_{wt}$ of the proppant leaving the mixer 110 is then determined according to the following:

$$PC_{wt} = (C_{wt} * D_{CL})/(1 - C_{wt}) \quad \text{(Eq. 18)}$$

This process of determining dry proppant concentration by volume or weight can be performed "on-the-fly" as a continuous process or periodically at different times. Knowing the dry proppant concentration, $PC_{wt}$, or $PC_{vol}$, the control system 150 can adjust the proppant metering device 116 to control the amount of proppant being delivered to the mixer 110. The determined dry proppant concentration can also be used to validate proppant concentration values supplied by a third party or third party proppant metering device without directly measuring delivery rate. In addition to adjusting the proppant metering device 116, the control system 150 may generate an indication, such as, but not limited to, an audible alarm, a message on a display, an electronic communication, such as a text message or an email, or any combination thereof to alert an operator of when the proppant concentration is not at a desired level or within a desired range. The determined dry proppant method also provides an accurate proppant concentration without requiring a RA densometer or other dedicated density measurement device.

In addition to determining dry proppant concentration, the control system 150 also determines the density of the fracturing fluid leaving the mixer, $D_2$, according to the following. First, $Q_{TL}$, the total liquid volumetric flow rate entering the mixer 110 is determined according to the following:

$$Q_{TL} = Q_1 + Q_{3F} \quad \text{(Eq. 19)}$$

The density of the fracturing fluid leaving the mixer, $D_2$, is then determined according to:

$$D_2 = (Q_{TL} * D_{CL} + MR_{DP})/Q_2 \quad \text{(Eq. 20)}$$

Figure 2:
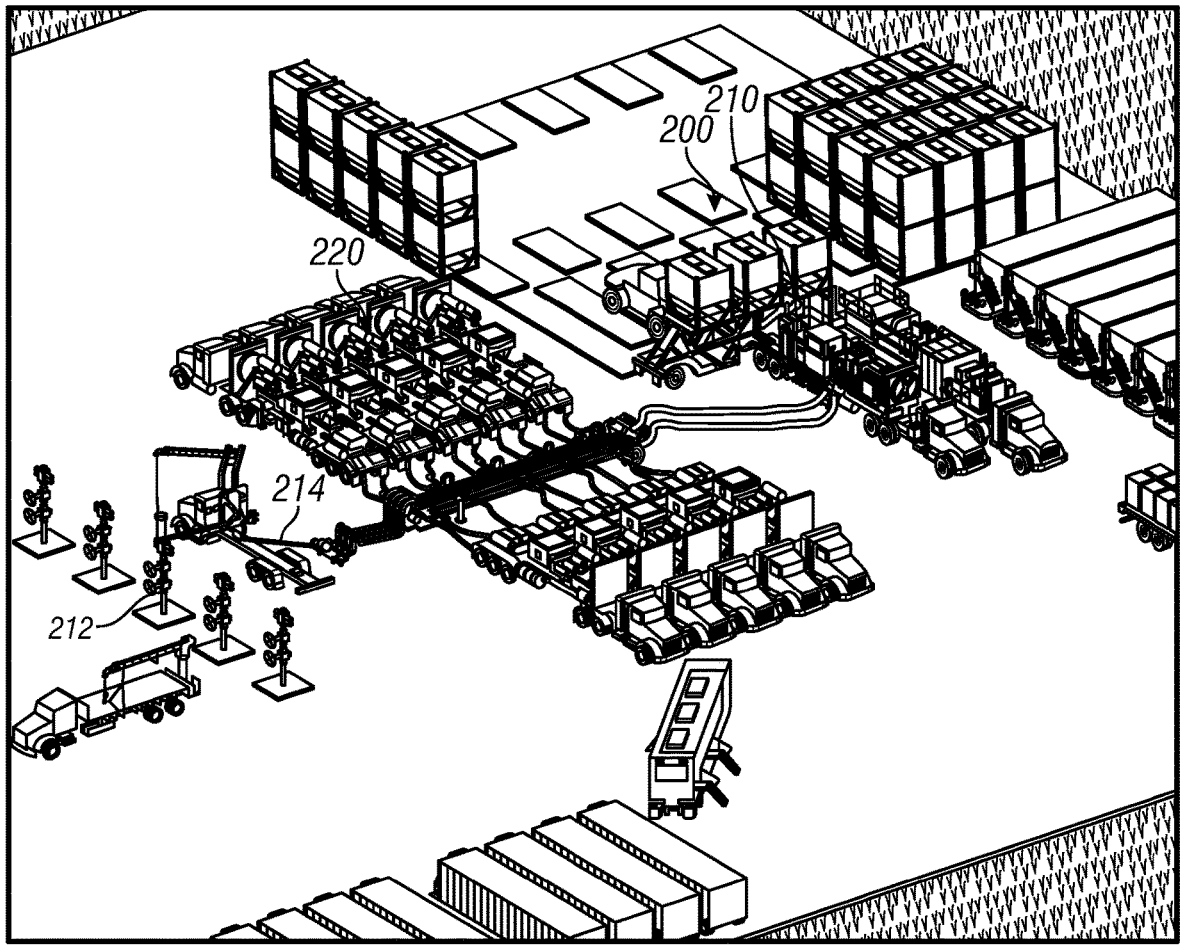
FIG. 2 is a schematic diagram of the treatment assembly of FIG. 1.

FIG. 2 shows an illustrative schematic of systems and apparatuses that can deliver the fracturing fluid to a subterranean location. It should be noted that while FIG. 2 generally depicts a land-based system or apparatus, like systems and apparatuses may be operated for subsea locations as well. As depicted in FIG. 2, a system or apparatus 200, such as the blending system described above, can include a mixer 210, in which the carrier fluid and the wet proppant are combined to form the fracturing fluid as described above. The fracturing fluid can be conveyed via a line 214 to the wellhead 212, where the fracturing fluid enters a tubular extending from the wellhead 212 into a subterranean formation. Upon being ejected from the tubular, the treatment fluid can subsequently penetrate into subterranean formation. The frac pumps 220 are operable at variable flow rates to regulate the pressure of the fracturing fluid for introduction into the tubular 216 and the formation 218. It is to be recognized that system or apparatus 200 is merely exemplary in nature and various additional components can be present that have not necessarily been depicted in FIG. 2 in the interest of clarity. In some examples, additional components that can be present include supply hoppers, valves, adapters, joints, gauges, sensors, pressure controllers, pressure sensors, flow rate controllers, flow rate sensors, temperature sensors, and the like.

Figure 3:
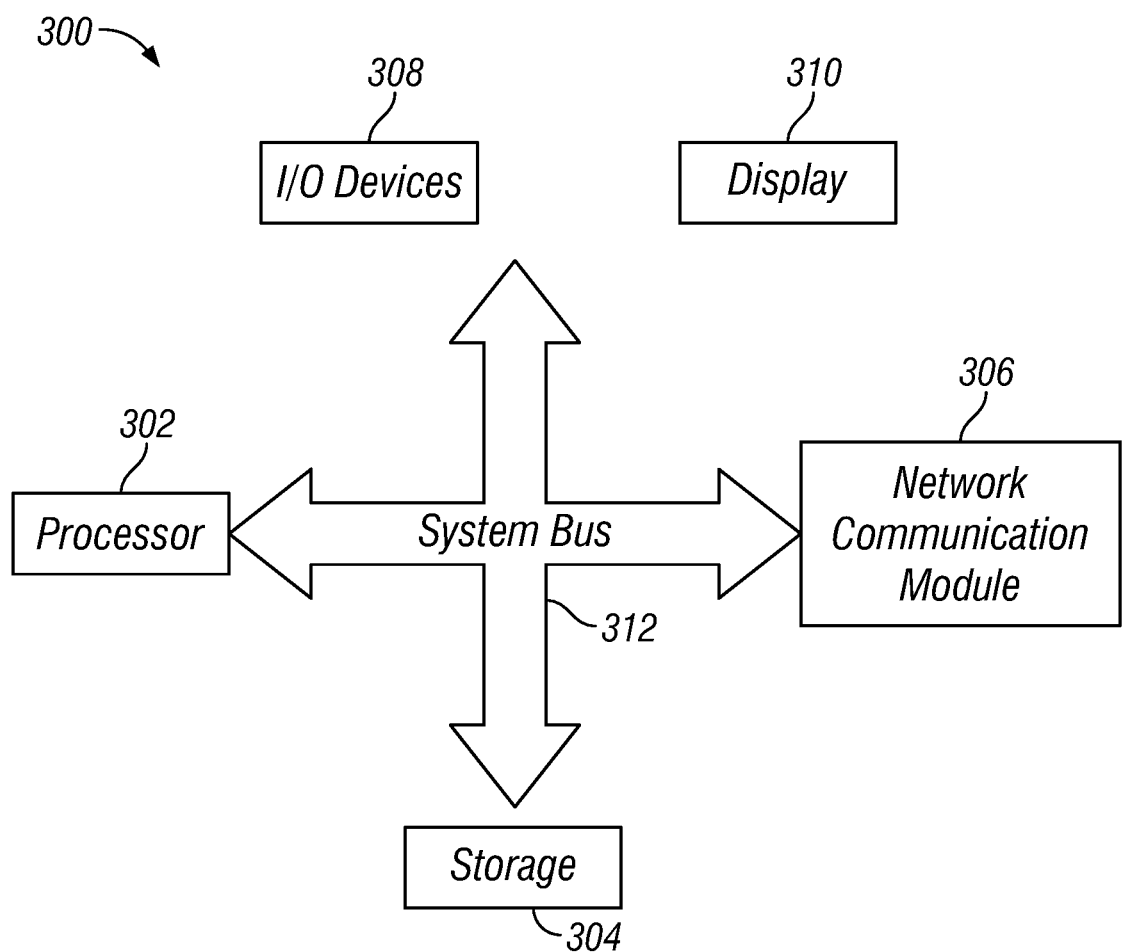
FIG. 3 is a diagram of a computer system usable by a treatment assembly, according to one or more embodiments.

Turning now to FIG. 3, FIG. 3 is a computer system 300 usable by a control system, such as the control system 150 described above, in controlling the operating mode of the treatment assembly 100. Additionally, the computer system 300 or a similar computer system may be utilized by a control system to control well completion operations, such as hydraulic fracturing. The computer system 300 includes at least one processor 302, a non-transitory, computer-readable storage 304, a transceiver/network communication module 306, optional input/output devices 308, and an optional display 310 all interconnected via a system bus 312. Software instructions executable by the processor 302 for implementing software instructions stored within the computer system 300 in accordance with the illustrative embodiments described herein, may be stored in the storage 304 or some other non-transitory computer-readable medium.

Although not explicitly shown in FIG. 3, it will be recognized that the computer system 300 may be connected to one or more public and/or private networks via appropriate network connections. It will also be recognized that software instructions may also be loaded into the storage 304 from a CD-ROM or other appropriate storage media via wired or wireless means.

For the embodiments and examples above, a non-transitory computer readable medium can comprise instructions stored thereon, which, when performed by a machine, cause the machine to perform operations, the operations comprising one or more features similar or identical to features of methods and techniques described above. The physical structures of such instructions may be operated on by one or more processors. A system to implement the described algorithm may also include an electronic apparatus and a communications unit. The system may also include a bus, where the bus provides electrical conductivity among the components of the system. The bus can include an address bus, a data bus, and a control bus, each independently configured. The bus can also use common conductive lines for providing one or more of address, data, or control, the use of which can be regulated by the one or more processors. The bus can be configured such that the components of the system can be distributed. The bus may also be arranged as part of a communication network allowing communication with control sites situated remotely from system.

A machine-readable signal medium may include a propagated data signal with machine-readable program code embodied therein, for example, in baseband or as part of a carrier wave. Such a propagated signal may take any of a variety of forms, including, but not limited to, electromagnetic, optical, or any suitable combination thereof. A machine-readable signal medium may be any machine-readable medium that is not a machine-readable storage medium and that can communicate, propagate, or transport a program for use by or in connection with an instruction execution system, apparatus, or device.

Program code embodied on a machine-readable medium may be transmitted using any appropriate medium, including but not limited to wireless, wireline, optical fiber cable, RF, etc., or any suitable combination of the foregoing.

Computer program code for carrying out operations for aspects of the disclosure may be written in any combination of one or more programming languages, including an object oriented programming language, a dynamic programming language, a scripting language, and conventional procedural programming languages. The program code may execute entirely on a stand-alone machine, may execute in a distributed manner across multiple machines, and may execute on one machine while providing results and or accepting input on another machine.

The program code/instructions may also be stored in a machine-readable medium that can direct a machine to function in a particular manner, such that the instructions stored in the machine-readable medium produce an article of manufacture including instructions which implement the function/act specified.

Peripheral devices such as displays, additional storage memory, and/or other control devices that may operate in conjunction with the one or more processors and/or the memory modules. The peripheral devices can be arranged to operate in conjunction with display unit(s) with instructions stored in the memory module to implement the user interface to manage the display of the anomalies. Such a user interface can be operated in conjunction with the communications unit and the bus. Various components of the system can be integrated such that processing identical to or similar to the processing schemes can be performed.

discharge rate. In Scenario 2, neglecting moisture leads to calculating the proppant concentration at 18.5 lb/gal, a 54% error. Thus, failing to correctly determine the dry proppant concentration can result in an error of up to at least 54%.

Figure 4:
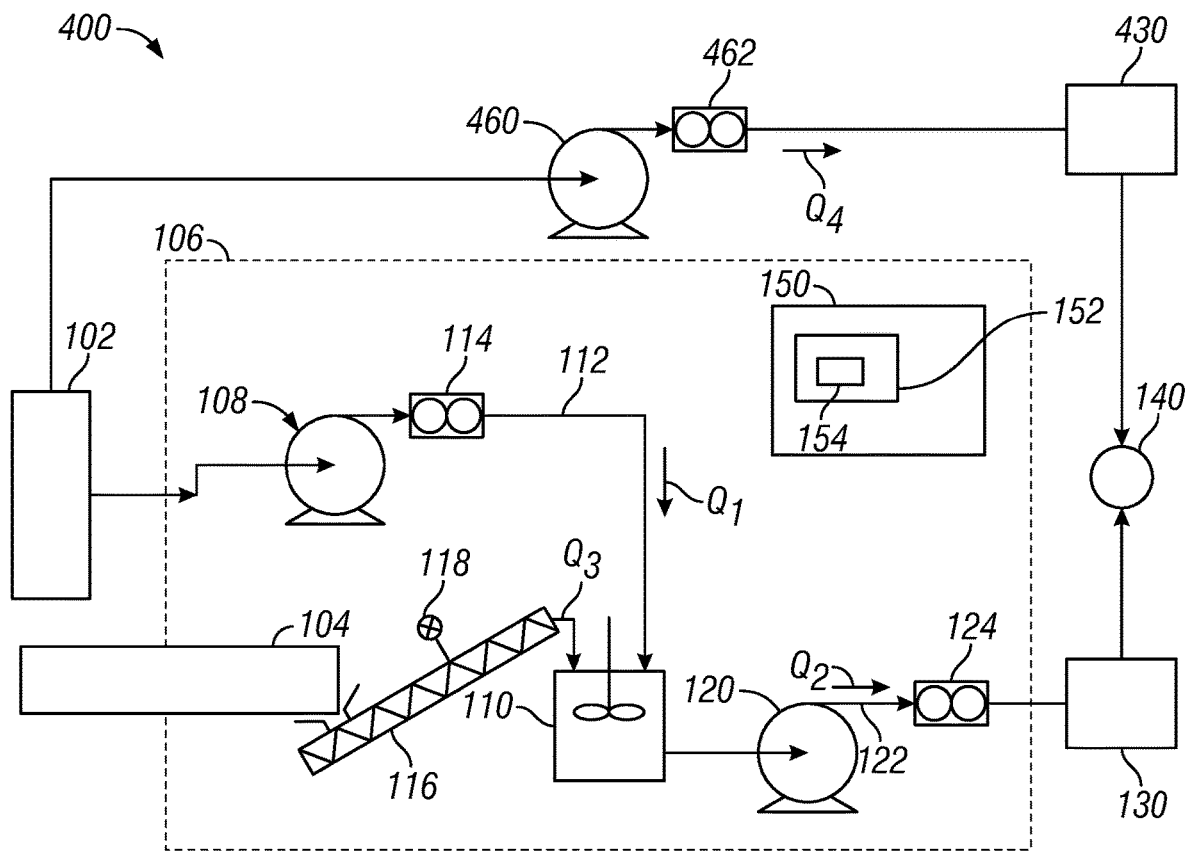
FIG. 4 is a block diagram of another embodiment of a treatment assembly used for conducting a treatment operation such a fracturing operation.

FIG. 4 is a block diagram of another embodiment of a treatment assembly 400 used for conducting a treatment operation such as a fracturing operation. The treatment assembly 400 includes much of the same equipment as the treatment assembly 100, such as aa "clean" fluid supply 102 for supplying a clean carrier fluid substantially free of any proppant. The treatment assembly 400 also includes a wet proppant supply 104 for supplying proppant that may be dampened with a dampening liquid. Both the carrier fluid and the wet proppant are supplied to a blending system 106 for blending the carrier fluid and the wet proppant into a fracturing fluid. The carrier fluid is pumped into the blending system 106 with a suction pump 108, which then pumps the carrier fluid into a mixer 110 through a conduit 112. Positioned at the suction pump 108 or within the conduit 112 is a flowmeter 114 operable to measure a flow rate $Q_1$ of the carrier fluid entering the mixer 110.

The wet proppant is moved by a proppant metering device 116, which delivers the wet proppant to the mixer 110 to be mixed with the carrier fluid to form the fracturing fluid. The proppant metering device is controllable to control the rate $Q_3$ of wet proppant delivered into the mixer 110. A moisture sensor or meter 118 may be installed on the proppant metering device 116 and is operable to determine a percent moisture by either weight or volume for the proppant entering the mixer 110. Alternatively, the moisture meter 118 may be installed at any point suitable to measure the percent moisture of the wet proppant before the wet proppant enters the mixer 110. Alternatively, the percent moisture content by either weight or volume may be inputted by a user.

With the wet proppant and the carrier fluid added to the mixer 110, the mixer 110 mixes the wet proppant and the

EXAMPLE

TABLE 1

| Variable | Units | Scenario 1: 2 lb/gal at 100 bpm 10% moisture content | | | Scenario 2: 12 lb/gal at 25 bpm 10% moisture content | | |
|---|---|---|---|---|---|---|---|
| MC | % by weigth | 10% | | | 10% | | |
| $Q_1$ | gal/min | 3749 | | | 572 | | |
| $Q_2$ | gal/min | 4200 | | | 1050 | | |
| DF | lb/gal | 8.33 | | | 8.33 | | |
| AVF | gal/lb | 0.0453 | | | 0.0453 | | |
| $Q_{3T}$ | gal/min | 451 | | | 478 | | |
| | | Accounting for moisture | Not accounting for moisture | | Accounting for moisture | Not accounting for moisture | |
| $Q_{3F}$ | gal/min | 103 | 0 | | 109 | 0 | |
| $Q_{3S}$ | gal/min | 348 | 451 | | 369 | 478 | |
| $Q_{TL}$ | gal/min | 3852 | 3749 | | 681 | 572 | |
| $MR_{DS}$ | lb/min | 7691 | 9956 | Error | 8152 | 10552 | Error |
| SC | lb/gal | 2.00 | 2.66 | 33% | 11.97 | 18.45 | 54% |

If the moisture content is not taken into account, the sand concentration calculation underestimates the liquid rate and overestimates sand rate, leading to a calculated sand concentration that is erroneously high. Table 1 demonstrates the error for two scenarios. In Scenario 1, the calculation is made for a 2 lb/gal sand concentration at 100 bpm, a typical rate and proppant concentration for a conventional fracture treatment). If the proppant has a moisture content of 10%, the conventionally calculated dry proppant concentration would be 2.7 lb/gal, a 33% error. Scenario 2 is the calculation for a 12 lb/gal proppant concentration at 25 bpm carrier fluid together into a fracturing fluid as described above. The bending system 106 further includes a discharge pump 120, which pumps the fracturing fluid out of the mixer 110 and out of the blending system 106 to one or more frac pumps 130 through a conduit 122. Positioned at the discharge pump 120 or within the conduit 122 is a flowmeter 124 operable to measure a flow rate $Q_2$ of the fracturing fluid flowing from the discharge pump 120 to the frac pumps 130. Alternatively, multiple flowmeters 124 may be located and operable to measure the flow rate outputs of the frac pumps 130 and the flow rate $Q_2$ determined by summing the measured flow rate outputs of the frac pumps 130.

The treatment assembly 400 also includes a clean boost pump 460 that accepts clean carrier fluid directly from the clean fluid supply 102 in a split flow process. In the split flow process, clean carrier fluid can flow to one or the other of the blender 106 or the clean boost pump 460 or both at the same time. A flow meter 462 positioned at the clean boost pump 460 is operable to measure a flow rate $Q_4$ of the clean carrier fluid exiting the clean boost pump 460 and flowing to additional frac pumps 430. The frac pumps 130 and 430 then pump the fracturing fluid into the borehole 140, typically through a wellhead, for delivery to the subterranean formation at pressure to create the conductive flow paths in the formation.

The treatment assembly 400 and operation thereof can be carried out using a computer-operated control system 150 as described above that includes a computer 152, which includes a processor 154. As mentioned above, the proppant metering device 116 is controllable to control the rate $Q_3$ of wet proppant delivered to the mixer 110. The control system 150 uses information received by the sensors or users and meters to determine the actual amount of proppant, or dry proppant, in the wet proppant and controls the wet proppant delivery rate $Q_3$ based on a desired dry proppant concentration in the fracturing fluid to be injected in the borehole. To do so, the control system 150 uses the computer 152 and the processor 152 to determine the dry proppant concentration in the fracturing fluid using the inputted or measured moisture content from the moisture meter 118 as described above. Doing so prevents overestimation of the dry proppant concentration and thus prevents using too much proppant in the fracturing fluid than is desired.

When the split flow process is used, the proppant concentration of the diluted fracturing fluid (fracturing fluid from the blender 106 and the clean carrier fluid from the clean boost pump) entering the borehole 140 through the well head must be calculated in addition to the proppant concentration of the fracturing fluid exiting the blender 106. The density of the diluted fracturing fluid would also be calculated.

The dry proppant concentration, $SC_{WH}$, at the well head using the split flow process can be determined according to the following:

$$SC_{WH} = MR_{DP}/(Q_{TL}+Q_4) \quad (Eq. 21)$$

The density of the diluted fracturing fluid, $D_{WH}$, at the well head using the split flow process can be determined according to the following:

$$D_{WH} = (Q_{TL}*D_{CL}+Q_4*D_1+MR_{DP})/(Q_2+Q_4) \quad (Eq. 22)$$

Knowing the dry proppant concentration and the density of the diluted fracturing fluid at the well head allows the control system 150 to control the wet proppant delivery rate, $Q_3$, based on a desired dry proppant concentration or density in the diluted fracturing fluid to be injected in the borehole 140.

Examples of the above embodiments include the following numbered examples, which may be combined together:

Example 1. A method of determining a dry proppant concentration in a fracturing fluid, comprising; combining a wet proppant with a carrier fluid in a mixer to form the fracturing fluid; and determining the dry proppant concentration of the fracturing fluid leaving the mixer using a moisture content of the wet proppant entering the mixer, wherein use of the moisture content prevents overestimation of the dry proppant concentration.

Example 2, the method of example 1, further comprising determining a density of the fracturing fluid leaving the mixer.

Example 3. The method of Example 1, wherein the moisture content is determined by measuring the moisture content with a moisture meter before combining the wet proppant with the carrier fluid to form the fracturing fluid.

Example 4. The method of Example 1, wherein the moisture content is received by an operator inputting a value.

Example 5. The method of Example 1, wherein determining the dry proppant concentration in the fracturing fluid using the moisture content is performed without measuring a flow rate of the wet proppant.

Example 6. The method of Example 1, further comprising repeating the determining moisture content, combining, and determining dry proppant concentration to determine the dry proppant concentration at different times.

Example 7. The method of Example 1, wherein determining the dry proppant concentration in the fracturing fluid using the moisture content comprises: determining a flow rate of the carrier fluid entering the mixer; determining a flow rate of the fracturing fluid leaving the mixer; and determining an absolute volume factor of the dry proppant in the fracturing fluid.

Example 8. The method of Example 7, wherein if the moisture content of the wet proppant is determined on a volumetric basis, the method further comprising determining a flow rate of a dampening fluid on the wet proppant according to:

$$Q_{3Fvol} = Q_{3Tvol} \times MC_{vol},$$

wherein $Q_{3Fvol}$ is the volumetric flow rate of the dampening liquid, $Q_{3Tvol}$ is the wet proppant volumetric flow rate, and $MC_{vol}$ is the moisture content expressed in vol %.

Example 9. The method of Example 7, wherein if the moisture content of the wet proppant is determined on a weight basis, the method further comprising determining a flow rate of the dampening liquid according to:

$$Q_{3F} = (Q_3*MC_{wt})/(MC_{wt}+DF*AVF(1-MC_{wt})),$$

wherein $Q_{3F}$ is the flow rate of the dampening liquid, $Q_3$ is the wet proppant flow rate, $MC_{wt}$ is the moisture content expressed in wt %, DF is a density of the dampening liquid, and AVF is an absolute volume factor of the dry proppant.

Example 10. The method of Example 7 further comprising determining a flow rate of the wet proppant entering the mixer by subtracting a flow rate of the carrier fluid from a flow rate of the fracturing fluid and subtracting a mixer change rate from the flow rate of the fracturing fluid.

Example 11. The method of Example 7, further comprising adjusting the flow rate of the wet proppant entering the mixer based on the determined dry proppant concentration or the density of the fracturing fluid.

Example 12. A system for injecting fracturing fluid into a borehole, the fracturing fluid comprising a carrier fluid mixed with a wet proppant comprising a dry proppant dampened with a dampening liquid, the system comprising: a mixer operable to receive and mix the carrier fluid and the wet proppant to form the fracturing fluid; a frac pump operable to inject the fracturing fluid into the borehole; and a control system comprising a processor operable to receive a moisture content of the wet proppant before being mixed with the carrier fluid and programmed to determine a dry proppant concentration of the fracturing fluid formed in the mixer using a moisture content of the wet proppant, wherein use of the moisture content prevents overestimation of the dry proppant concentration.

Example 13. The system of Example 12, wherein the processor is further programmed to determine a density of the fracturing fluid.

Example 14. The system of Example 12, wherein the moisture content of the wet proppant before being mixed with the carrier fluid is either measured with a moisture meter before the wet proppant and the carrier fluid are mixed to form the fracturing fluid or is inputted into the control system by an operator.

Example 15. The system of Example 12, wherein the processor is further programmed to determine the dry proppant concentration in the fracturing fluid using the moisture content without using a measured flow rate of the wet proppant into the mixer.

Example 16. The system of Example 12, wherein the processor is programmed to determine the dry proppant concentration in the fracturing fluid using the moisture content further comprises: determining a flow rate of the carrier fluid entering the mixer; determining a flow rate of the fracturing fluid leaving the mixer; and determining an absolute volume factor of the dry proppant in the fracturing fluid.

Example 17. The system of Example 12, further comprising wherein the processor is programmed to adjust the flow rate of the wet proppant entering the mixer based on the determined dry proppant concentration or density of the fracturing fluid.

Example 18. A method of injecting a fracturing fluid into a borehole, comprising: combining a carrier fluid with a wet proppant comprising a dry proppant dampened with a dampening liquid in a mixer to form the fracturing fluid; determining a dry proppant concentration of the fracturing fluid formed in the mixer using a moisture content of the wet proppant, wherein use of the moisture content prevents overestimation of the dry proppant concentration; and injecting the fracturing fluid in a borehole.

Example 19. The method of Example 18, further comprising determining a density of the fracturing fluid formed in the mixer.

Example 20. The method of Example 18, wherein determining the dry proppant concentration in the fracturing fluid using the moisture content is performed without measuring a flow rate of the wet proppant.

Certain terms are used throughout the description and claims to refer to particular features or components. As one skilled in the art will appreciate, different persons may refer to the same feature or component by different names. This document does not intend to distinguish between components or features that differ in name but not function.

While compositions and methods are described herein in terms of "comprising" various components or steps, the compositions and methods can also "consist essentially of" or "consist of" the various components and steps.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments. At the very least, and not as an attempt to limit the application of the doctrine of equivalents to the scope of the claim, each numerical parameter should at least be construed in light of the number of reported significant digits and by applying ordinary rounding techniques accepted by those skilled in the art.

The embodiments disclosed should not be interpreted, or otherwise used, as limiting the scope of the disclosure, including the claims. It is to be fully recognized that the different teachings of the embodiments discussed may be employed separately or in any suitable combination to produce desired results. In addition, one skilled in the art will understand that the description has broad application, and the discussion of any embodiment is meant only to be exemplary of that embodiment, and not intended to suggest that the scope of the disclosure, including the claims, is limited to that embodiment.

What is claimed is:

1. A method of determining a dry proppant concentration in a fracturing fluid, comprising;
    combining a wet proppant with a carrier fluid in a mixer to form the fracturing fluid; and
    determining the dry proppant concentration of the fracturing fluid leaving the mixer using a moisture content of the wet proppant entering the mixer, wherein use of the moisture content prevents overestimation of the dry proppant concentration.

2. The method of claim 1, further comprising determining a density of the fracturing fluid leaving the mixer.

3. The method of claim 1, wherein the moisture content is determined by measuring the moisture content with a moisture meter before combining the wet proppant with the carrier fluid to form the fracturing fluid.

4. The method of claim 1, wherein the moisture content is received by an operator inputting a value.

5. The method of claim 1, wherein determining the dry proppant concentration in the fracturing fluid using the moisture content is performed without measuring a flow rate of the wet proppant.

6. The method of claim 1, further comprising repeating the determining moisture content, combining, and determining dry proppant concentration to determine the dry proppant concentration at different times.

7. The method of claim 1, wherein determining the dry proppant concentration in the fracturing fluid using the moisture content comprises:
    determining a flow rate of the carrier fluid entering the mixer;
    determining a flow rate of the fracturing fluid leaving the mixer; and
    determining an absolute volume factor of the dry proppant in the fracturing fluid.

8. The method of claim 7, wherein if the moisture content of the wet proppant is determined on a volumetric basis, the method further comprising determining a flow rate of a dampening fluid on the wet proppant according to:

$$Q_{3Fvol} = Q_{3Tvol} \times MC_{vol},$$

wherein $Q_{3Fvol}$ is the volumetric flow rate of the dampening liquid, $Q_{3Tvol}$ is the wet proppant volumetric flow rate, and $MC_{vol}$ is the moisture content expressed in vol %.

9. The method of claim 7, wherein if the moisture content of the wet proppant is determined on a weight basis, the method further comprising determining a flow rate of the dampening liquid according to:

$$Q_{3F} = (Q_3 * MC_{wt})/(MC_{wt} + DF * AVF(1 - MC_{wt})),$$

wherein $Q_{3F}$ is the flow rate of the dampening liquid, $Q_3$ is the wet proppant flow rate, $MC_{wt}$ the moisture content expressed in wt %, DF is a density of the dampening liquid, and AVF is an absolute volume factor of the dry proppant.

10. The method of claim 7 further comprising determining a flow rate of the wet proppant entering the mixer by subtracting a flow rate of the carrier fluid from a flow rate of the fracturing fluid and subtracting a mixer change rate from the flow rate of the fracturing fluid.

11. The method of claim 7, further comprising adjusting the flow rate of the wet proppant entering the mixer based on the determined dry proppant concentration or the density of the fracturing fluid.

12. A system for injecting fracturing fluid into a borehole, the fracturing fluid comprising a carrier fluid mixed with a wet proppant comprising a dry proppant dampened with a dampening liquid, the system comprising:
    a mixer operable to receive and mix the carrier fluid and the wet proppant to form the fracturing fluid;
    a frac pump operable to inject the fracturing fluid into the borehole; and
    a control system comprising a processor operable to receive a moisture content of the wet proppant before being mixed with the carrier fluid and programmed to determine a dry proppant concentration of the fracturing fluid formed in the mixer using a moisture content of the wet proppant, wherein use of the moisture content prevents overestimation of the dry proppant concentration.

13. The system of claim 12, wherein the processor is further programmed to determine a density of the fracturing fluid.

14. The system of claim 12, wherein the moisture content of the wet proppant before being mixed with the carrier fluid is either measured with a moisture meter before the wet proppant and the carrier fluid are mixed to form the fracturing fluid or is inputted into the control system by an operator.

15. The system of claim 12, wherein the processor is further programmed to determine the dry proppant concentration in the fracturing fluid using the moisture content without using a measured flow rate of the wet proppant into the mixer.

16. The system of claim 12, wherein the processor is programmed to determine the dry proppant concentration in the fracturing fluid using the moisture content further comprises:
    determining a flow rate of the carrier fluid entering the mixer;
    determining a flow rate of the fracturing fluid leaving the mixer; and
    determining an absolute volume factor of the dry proppant in the fracturing fluid.

17. The system of claim 12, further comprising wherein the processor is programmed to adjust the flow rate of the wet proppant entering the mixer based on the determined dry proppant concentration or density of the fracturing fluid.

18. A method of injecting a fracturing fluid into a borehole, comprising:
    combining a carrier fluid with a wet proppant comprising a dry proppant dampened with a dampening liquid in a mixer to form the fracturing fluid;
    determining a dry proppant concentration of the fracturing fluid formed in the mixer using a moisture content of the wet proppant, wherein use of the moisture content prevents overestimation of the dry proppant concentration; and
    injecting the fracturing fluid in a borehole.

19. The method of claim 18, further comprising determining a density of the fracturing fluid formed in the mixer.

20. The method of claim 18, wherein determining the dry proppant concentration in the fracturing fluid using the moisture content is performed without measuring a flow rate of the wet proppant.

* * * * *